(12) United States Patent
Cuero et al.

(10) Patent No.: US 9,987,219 B2
(45) Date of Patent: Jun. 5, 2018

(54) UV-RESISTANT MICROBES AND UV-BLOCKING MICROBIAL EXTRACT

(71) Applicants: The Texas A&M University System, College Station, TX (US); The United States of America as represented by the Administrator of the National Aeronautics and Space Administration, Washington, DC (US)

(72) Inventors: Raul G. Cuero, Cypress, TX (US); David S. McKay, Friendswood, TX (US)

(73) Assignee: THE TEXAS A&M UNIVERSITY SYSTEM, College Station, TX (US)

(*) Notice: Subject to any disclaimer, the term of this patent is extended or adjusted under 35 U.S.C. 154(b) by 0 days. days.

(21) Appl. No.: 15/692,066

(22) Filed: Aug. 31, 2017

(65) Prior Publication Data

US 2017/0360695 A1    Dec. 21, 2017

Related U.S. Application Data

(63) Continuation of application No. 15/406,167, filed on Jan. 13, 2017, which is a continuation of application No. 14/105,543, filed on Dec. 13, 2013.

(60) Provisional application No. 61/738,117, filed on Dec. 17, 2012.

(51) Int. Cl.
  *A61K 8/99* (2017.01)
  *A01N 63/04* (2006.01)
  *A61Q 17/04* (2006.01)
  *A01N 63/02* (2006.01)

(52) U.S. Cl.
  CPC .............. *A61K 8/99* (2013.01); *A01N 63/02* (2013.01); *A01N 63/04* (2013.01); *A61Q 17/04* (2013.01)

(58) Field of Classification Search
  CPC .......... A01N 63/02; A01N 63/04; A61K 8/99; A61Q 17/04
  See application file for complete search history.

(56) References Cited

U.S. PATENT DOCUMENTS

| | | |
|---|---|---|
| 5,643,587 A | 7/1997 | Scancarella et al. |
| 6,379,964 B1 | 4/2002 | del Cardayre et al. |
| 2009/0035864 A1 | 2/2009 | Parada et al. |
| 2010/0192261 A1 | 7/2010 | Kwok et al. |
| 2011/0117641 A1 | 5/2011 | Jia |
| 2012/0026390 A1 | 2/2012 | Matsuhira |

OTHER PUBLICATIONS

Hanson, et al. (Rna, 2005, vol. 11, pp. 503-511).
Eurasyp (European Association for Specialty Yeast Products, www.yeastextract.info, printed 2016).
Vilber (VL-6.0 UV lamp information, printed 2016).
Hahn lan (Yeast Whole Cell Extract protocol, http://research.fhcrc.org/content/dam/stripe/hahn/methods/biochem/Improved%20Yeast%20Whole%20Cell%20Extract%20Methods.pdf, printed 2016).
Ausubel, et al. (Current Protocols in Molecular Biology, 2003, pp. 13.13.3-13.13.9).
Radovic, et al. (Yeast Research, 2007, vol. 7, pp. 527-539).
International Search Report and Written Opinion; PCT/US2013/75238; pp. 11, dated May 16, 2014.
Bhattacharyya et al. "Enhanced UV Sensitivity of Thiobacillus ferrooxidans Resulting from Caffeine and Acriflavine Treatment of Irradiated Cells"; Current Microbiology, vol. 43; pp. 149-153, 2001.
Ohmura, et al. (Journal of Bacteriology, 2002, vol. 184, pp. 2081-2087).

*Primary Examiner* — Mark V Stevens
(74) *Attorney, Agent, or Firm* — Baker Botts L.L.P.

(57) ABSTRACT

The present disclosure relates to a composition including an extract from an *Acidithiobacillus* bacteria or a yeast extracted after exposure of the bacteria to UV radiation. The disclosure further relates to a method of preparing a UV-blocking composition by exposing a culture of *Acidithiobacillus* or yeast to UV radiation and extracting UV-blocking cellular material produced in response to the UV radiation from the *Acidithiobacillus* or yeast. The disclosure further relates to a method of protecting an item from UV radiation damage by extracting UV-blocking cellular material from *Acidithiobacillus* or yeast exposed to UV radiation and covering the item with the UV-blocking cellular material. The disclosure further relates to a UV-resistant yeast cell and a UV-resistant bacterial cell.

17 Claims, 1 Drawing Sheet

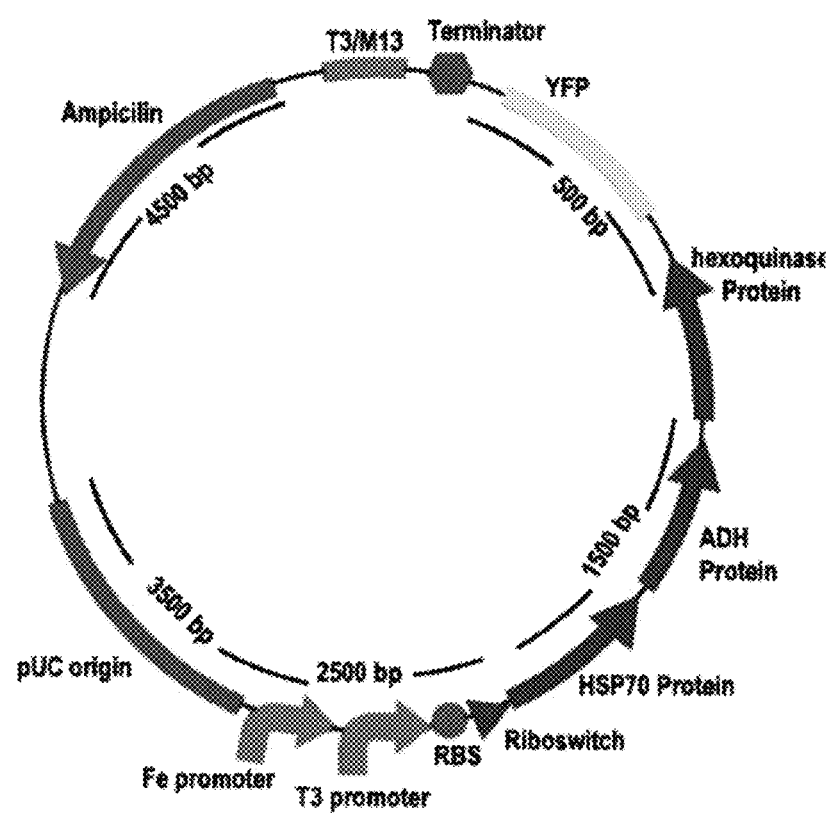

UV-RESISTANT MICROBES AND UV-BLOCKING MICROBIAL EXTRACT

PRIORITY CLAIM

The present application is a continuation of pending U.S. patent application Ser. No. 15/406,167 filed Jan. 13, 2017; which is a continuation of U.S. patent application Ser. No. 14/105,543 filed Dec. 13, 2013, now abandoned; which claims priority under 35. U.S.C. § 119 to U.S. Provisional Patent Application Ser. No. 61/738,117, filed Dec. 17, 2012, the contents of which are incorporate by reference herein in their entirety.

STATEMENT OF GOVERNMENT INTEREST

Portions of the current invention were developed using US government funding provided under NASA-NAG 9-1241 and SynBERC-NSF-University of California-Berkeley-1385638, and by the USDA under Evans-Allen-Prairie View grant 2011-33100-8916. Accordingly, the US government has certain rights in the invention. The invention described herein was also made by an employee of the United States Government and may be manufactured and used by or for the Government of the United States of America for governmental purposes without the payment of any royalties thereon or therefor.

REFERENCE TO SEQUENCE LISTING SUBMITTED VIA EFS-WEB

This application includes an electronically submitted sequence listing in .txt format. The .txt file contains a sequence listing entitled "2017-04-27 017575.1578_ST25.txt" created on Apr. 27, 2017 and is 5,996 bytes in size. The sequence listing contained in this .txt file is part of the specification and is hereby incorporated by reference herein in its entirety.

TECHNICAL FIELD

The present disclosure relates to engineered microbes, such as bacteria and yeast, that are resistant to ultraviolet (UV) radiation damage. The present disclosure also relates to UV-protective microbial extracts that may be prepared from such engineered microbes or from microbes exposed to UV radiation. The disclosure further relates to methods using these microbes or extracts, such as fermentation processes and methods of protecting agricultural plants or other materials from UV radiation.

BACKGROUND

Exposure to UV radiation causes harmful effects in a wide variety of things, both living and non-living. For example, exposure of human skin to UV radiation can cause sever sunburn and skin cancer and exposure of beneficial microorganisms to UV radiation can kill them. UV radiation can also cause materials to degrade prematurely and thus suffer mechanical failure or otherwise become unable to serve their intended purpose.

The harmful effects of UV radiation can generally be prevented to lessened through the simple step of absorbing all or a portion of UV radiation before it reaches the thing it may harm. For, example, chemicals in sunscreen absorb a portion of the UV radiation that would normally reach the skin and, as a result, help protect the skin from sunburn and skin cancer.

Although numerous substances able to absorb UV radiation are known, not all of them are suitable for all possible uses. Further, some substances may be expensive to produce or may have harmful side effects, such as toxicity or undesired chemical reactions with a protected material. Other substances simply do not last long enough in the environment in which they are used or last too long.

Accordingly, there is a demand for new substances able to absorb UV radiation, particularly if those substances are biocompatible.

SUMMARY

The present disclosure relates to a composition including an extract from an *Acidithiobacillus* bacteria or a yeast extracted after exposure of the bacteria to UV radiation.

The disclosure further relates to a method of preparing a UV-blocking composition by exposing a culture of *Acidithiobacillus* or yeast to UV radiation and extracting UV-blocking cellular material produced in response to the UV radiation from the *Acidithiobacillus* or yeast.

The disclosure further relates to a method of protecting an item from UV radiation damage by extracting UV-blocking cellular material from *Acidithiobacillus* or yeast exposed to UV radiation and covering the item with the UV-blocking cellular material.

The disclosure further relates to a UV-resistant yeast cell including a plasmid comprising a nucleic acid encoding at least one of a Msn4pn, a ruvB, a heat shock protein, an alcohol dehydrogenase (ADH) protein, a NADH-cytochrome b5 reductase 2, a NADP-specific glutamate dehydrogenase, a superoxide dismutase, a hexokinase protein, or a phosphate glycerate mutase under control of a constitutive or inducible promoter.

The disclosure further relates to a UV-resistant bacterial cell including a plasmid comprising a nucleic acid encoding at least one of a major outer membrane protein, a RuBisCO large subunit 1 or 2, a phosphoribulokinase, a Ketol-acid reductoisomerase, a pyridine nucleotide-disulfide oxoreductase, a methionine synthase, or a methyltransferase under control of a constitutive or inducible promoter.

BRIEF DESCRIPTION OF THE DRAWINGS

Embodiments of the present invention may be better understood through reference to the following figures in which:

FIG. 1 illustrates a plasmid that may be used to produce and located in a UV-resistant yeast.

DETAILED DESCRIPTION

The present disclosure relates to engineered microbes, such as bacteria and yeast, that are resistant to ultraviolet (UV) radiation damage. The present disclosure also relates to UV-protective microbial extracts that may be prepared from such engineered microbes or from microbes exposed to UV radiation. The disclosure further relates to methods using these microbes or extracts, such as fermentation processes and methods of protecting agricultural plants or other materials from UV radiation.

UV-Protective Extracts

UV-protective microbial extracts of the present disclosure may be able to wholly or partially block the passage of UV radiation. The extent to which UV-radiation is blocked may depend on a variety of factors including the microbial source, the amount of extract applied, and the formulation of the extracts.

The UV-protective extract may be prepared by exposing a microbe culture, such as a bacteria or yeast culture, to UV radiation, then extracting components from the culture via centrifugation. The UV radiation may be of any wavelength, but in specific embodiments it may be short wave (254 nm), long wave (365 nm), or a combination of both. In one embodiment, a bacterial extract may be derived from *Acidithiobacillus*, particularly *A. ferroxidans*, after exposure of bacteria culture to UV radiation, foe example for at least 72 hours. In another embodiment, a yeast extract may be derived from *S. cerevisiae* or other yeast after exposure of yeast culture to UV radiation, for example for at least 48 hours. In still another embodiment, the extract may be prepared by culturing an engineered UV-resistant bacteria or yeast, such as a bacteria or yeast of the type described below, then extracting components from the culture via centrifugation.

According to one embodiment, extracts of the present disclosure may be prepared by culturing an *Acidithiobacillus*, such as *A. ferroxidans* or by culturing *S. cerevisiae* or other yeast. Culture may proceed until dense, but not so dense as to trigger deleterious responses such as those triggered by lack of a food source. The culture may also not be so dense as to prevent UV radiation from reaching a substantial portion of bacteria or yeast in the culture. The culture may then be irradiated with UV radiation. Prior to irradiation, the culture may be transferred to one or move vessels designed to allow a substantial portion of the bacteria or yeast to be irradiated. The wavelength of UV radiation may be any wavelength, but in particular embodiments may be selected to induce a radiation response in the bacteria or yeast. Similarly, the length of exposure to the UV radiation may be any length from the minimal amount needed to induce a radiation response in at least some bacteria or yeast of the culture up to a length of time at which a substantial portion of the bacteria or yeast in the culture are fatally irradiated.

After irradiation, the bacteria or yeast may continue to be cultured for a time at least sufficient to allow some radiation response in the bacteria or yeast. If the bacteria or yeast were irradiated in a manner that causes death of a substantial portion of the bacteria or yeast, culture may cease after the majority of this bacterial or yeast death has occurred. Alternatively, if the bacteria or yeast were not irradiated in such a manner as to cause death of a substantial portion of the bacteria or yeast, culture may continue until such time as the radiation response has ceased in a substantial portion of the bacteria or yeast.

Radiation response may include may include up-regulation in a yeast of at least one of the following: a Msn4pn, a ruvB, a heat shock protein, such as a heat shock protein SSB1, an alcohol dehydrogenase (ADH) protein, a NADH-cytochrome b5 reductase 2, a NADP-specific glutamate dehydrogenase, a superoxide dismutase, a hexokinase protein, such as hexokinase 1, or a phosphate glycerate mutase. Radiation response may include may include up-regulation in a bacterium of at least one of the following: a major outer membrane protein, such as major outer membrane protein 40, a RuBisCO large subunit 1 or 2, a phosphoribulokinase, a Ketol-acid reductoisomerase, a pyridine nucleotide-disulfide oxoreductase, a methionine synthase, a hydromethyl-transferase, a ribosomal protein s2, or a methyltransferase. Radiation response may additionally or alternatively include down-regulation in a yeast of at least one of the following: a protein disulfide isomerase, an alpha-glucosidase MAL12, a methyl tetrahydropteroyl triglutamate, a fructose-bisphosphate aldolase, or a glucokinase 1. Radiation response may additionally or alternatively include down-regulation in a bacterium of at least one of the following: a Hsp 20, a caperonin, chaperone protein Dnak, or a Hsp 70.

It will be understood that up-regulation or down-regulation of one or more of these proteins may not be directly responsible for UV-protective properties, such that increased or decreased amounts of these proteins in the extract may have little or no effect on its UV-protective properties. Rather, up-regulation or down-regulation of one of these proteins may have downstream effects that ultimately produce a UV-protective extract.

The extract may be prepared in manner able to isolate at least one UV-protective component. In particular embodiments, the extract may include centrifuged bacterial components. The extract may be formulated at a variety of concentrations in any acceptable carrier to allow its use for a particular purpose. In particular embodiments, the extract may be formulated in an evaporable carrier, such as water or alcohol, to allow the extract to dry on the surface of the material to be protected from UV radiation.

In one example, the extract may be prepared by centrifuging the bacteria or yeast culture in a manner able to precipitate most proteins, then discarding the supernatant while retaining the pellet as the extract. The pellet may then be used as is or dried. The pelleted material may be diluted to a given concentration using any acceptable carrier, such as water or alcohol. The carrier may be non-denaturing. The carrier may also include materials to inhibit further bacterial growth and/or protein degradation.

In an alternative example, the bacteria or yeast may not be pelletized but may instead be killed, for example by lysis or exposure to lethal levels of UV radiation, and the bacterial or yeast culture medium may be used as is or in an evaporated form. In this example materials to inhibit further bacterial or yeast growth and/or protein degradation may also be introduced.

In a further embodiment, isolated proteins from the bacteria or yeast culture may be used in place of a more general extract to produce the UV-protective effect. Such proteins may be isolated by further chemical extraction.

Use of UV-Protective Extract

The extract may be applied to any material that may benefit from a reduction in UV radiation. The exact formulation of the extract plus any carriers may be adjusted based on the desired use. For example, the extract may be formulated with only non-toxic components if it is to be used on a human or animal or with another microorganism, such as in a fermentation process or on an agricultural product. The extract may be mixed with other substances provide UV-protective properties to the overall composition. Further, if coated on the material to be protected, the extract may itself be covered with a further protective coating to protect, for example, against mechanical wear and damage.

The extract may be formulated or applied in such a manner as to block approximately 50%, 60%, 70%, 80%, 90%, 95%, or 99% of the UV radiation that encounters the extract. The extract may also be formulated to block these percentages of particular UV wavelengths, or, more generally, to block these percentages of longwave UV radiation or shortwave UV radiation.

Extracts according to the present disclosure may be used for a variety of purposes. These purposes include, but are not limited to the following:

1) blocking UV radiation or other types of radiation;
2) protecting human skin against damage and/or skin cancer induced by UV radiation or other types of radiation;
3) protecting against side-effects of radiation used in cancer treatments;
4) protecting animals from deleterious effects of UV radiation or other radiation;
5) protecting plastic, glass, or other solid surfaces from UV radiation or other radiation;
6) providing a UV radiation screen or screen for other types of radiation;
7) protecting astronauts and/or other persons or organisms as well as equipment during space trips;
8) enhancement of industrial fermentation processes or other processes requiring energy by allowing the use of UV radiation in connection with the process to supply additional energy and thus to increase the ultimate energy-requiring output of the cells, such as alcohol or a drug, without substantially killing the fermenting organism;
9) protection of experimentation, fermentation, biochemical, and/or biological processes under the presence of UV radiation, for example in extraterrestrial conditions such as on the Moon or Mars; and
10) protection of agricultural plants, particularly agricultural plants in which the revenue-producing product is located above-ground, such as fruits, vine-vegetables, beans and peas, and leaf vegetables.

In one particular embodiment, an extract according to the present disclosure, particularly an *A. ferroxidans* extract, may be applied to a fruit or vegetable, such as a watermelon or a tomato, during at least a part of its growth to increase the amounts of one or more nutrients of the fruit or vegetable, such as a vitamin, mineral, or other recommended dietary component. In one specific example, the amount of lycopene may be increased (which may be accompanied by a decrease in carotene or other less-valuable nutrients formed by competing pathways). In another specific embodiment, the amount of a flavor-enhancing component, such as glucose, may be increased. In another specific embodiment, a component beneficial to the plant may be increased. For example, an increase in glucose helps protect against water loss.

The extract may be applied for approximately 25%, 50%, 75%, 90% or 99% of the fruit or vegetable's on-plant life, where the on-plant life includes the time span from the formation of a separate body that will constitute the fruit or vegetable (excepting flowers) until the fruit or vegetable is harvested. In a specific embodiment, the extract may be first applied when the fruit or vegetable is sufficiently large to no longer be substantially protected from UV radiation by leaves. In another specific embodiment, the extract may first be applied five days, one week, or two weeks prior to harvest. This embodiment may be particularly useful with fruits or vegetables in which an increase in a nutrient or flavor-enhancing component may be obtained by protecting the fruit or vegetable from UV radiation later in its on-plant life.

The extract may be applied once or multiple times to each fruit or vegetable. For example, it may be applied weekly, or it may be reapplied after the fruit or vegetable is exposed to rain or after a turning process.

Application may be accomplished with a commercial sprayer. Application may be only one the upper portions of the fruit or vegetable, which are exposed to substantially greater amounts of UV radiation than lower portions of the fruit or vegetable.

UV-Resistant Microbes

According to another embodiment, a yeast or bacteria, particularly a beneficial yeast or bacteria such as one used in a fermentation process, may be engineered to be UV-resistant by transforming or transfecting the yeast or bacteria with a nucleic acid able to express a protein up-regulated by UV-exposure or with a nucleic acid able to ultimately cause a decrease in expression of a protein down-regulated by UV-exposure. These nucleic acids may be under the control of a constitutive promoter or under control of a UV-inducible promoter. Particularly in embodiments in which the yeast or bacteria needs to perform another function, such as fermentation, the nucleic acids may be under control of UV-inducible promoter so as not to impeded the other function when UV protection is not required.

In one specific embodiment, a yeast may be transfected with a nucleic acid encoding at least one of the following: a Msn4pn, a ruvB, a heat shock protein, such as a heat shock protein SSB1, an alcohol dehydrogenase (ADH) protein, a NADH-cytochrome b5 reductase 2, a NADP-specific glutamate dehydrogenase, a superoxide dismutase, a hexokinase protein, such as hexokinase 1, or a phosphate glycerate mutase. In another embodiment, a bacterium may be transformed with a nucleic acid encoding at least one of the following: a major outer membrane protein, such as major outer membrane protein 40, a RuBisCO large subunit 1 or 2, a phosphoribulokinase, a Ketol-acid reductoisomerase, a pyridine nucleotide-disulfide oxoreductase, a methionine synthase, or a methyltransferase.

Methods Using UV-Resistant Microbes

UV-resistant microbes may be used in fermentation processes, such as in the production of alcohol or fuel ethanol, or in the production of chemical and pharmaceutical products, including biological drug products.

EXAMPLES

The present disclosure may be better understood through reference to the following examples. These examples are included to describe exemplary embodiments only and should not be interpreted to encompass the entire breadth of the invention.

Example 1: Bacteria Culture and UV Exposure

*A. ferroxidans* (ATCC 13598) was grown in ATCC liquid medium #2039 Brown, following the ATCC recommendations. ATCC liquid medium #2039 Brown contains different ingredients including minerals salts such as Fe (II or III), Mg (II), Zn (II), Mn (II), Ca (II), Co (II), Cu (II), and other solutions such as $NaCl_2$, Nitrilotriacetico acid, $(NH_4)_2SO_4$, $AlK(SO_4)_2$, $H_3BO_3$, $Na_2MoO_4$. The medium was prepared based on 1 liter volume. Fifty mL of *A. ferroxidans* stock culture (1 month old) was transferred into 5 liters of ATCC liquid medium #2039, as above described, in a 6 liter flask. Two types of media were prepared, one containing Fe (II) and the other containing Fe (III), in addition to the other ingredients, as mentioned above. The flasks containing the *A. ferroxidans* cultures were covered with a spongy stopper, thus allowing oxygen penetration, and incubated at room temperature for 12 days.

After 12 days of incubation, two liters of *A. ferroxidans* cultures were transferred into OJO-sterilized glass trays (200 mL per each tray), aseptically. The trays containing the *A. ferroxidans* cultures were exposed to UV radiation at a short wavelength, 254 nm or a long wavelength, 365 nm for 0, 12, 24, 48, 72, 96 or 120 hours. Different trays were used per different type of iron (Fe II or Fe III) and for different lengths of time, as above described. Only two trays containing the *A. ferroxidans* cultures were used at a time. An ultraviolet fluorescent analysis cabinet (50 cm×50 cm×20 cm) (Spectroline model cc-80) was used for the UV irradiation.

TABLE 1 indicates the effect of the short wave UV irradiation (254 nm) on growth of the bacterium *A ferroxidans*. The results show that growth of the bacterium *A ferroxidans* was not significantly affected by the UV radiation, even after 48 hours of exposure. In fact, the biomass of *A. ferroxidans*, although showing an initial decrease, rebounded and was not significantly decreased as compared to the initial biomass after 24 hours of exposure to UV radiation. This biphasic growth is a typical growth pattern for *A. ferroxidans*. When growth is slower new medium and additional oxygen is typically required for growth to continue. The overall higher levels of biomass at 0.5 and 48 hours in the UV-exposed bacteria as compared to non-UV-exposed bacteria shows that the UV light can in fact provide additional energy to the fermentation process, allowing the bacteria to grow without the need for new medium or additional oxygen, or with less frequent addition of new medium or additional oxygen.

TABLE 1

Growth of Bacterium *A. Ferroxidans* (ATCC 13598) Under Exposure to UV Irradiation for Up To 2 Days

| Length of Exposure (Hour) | Bacterial Growth (biomass mg/L)[3] | | | |
|---|---|---|---|---|
| | No-UV (Control) | | UV[2] | |
| | Trials[1] | Average | Trials | Average |
| 0 | 250 + 250 + 250 | 250 | 250 + 250 + 250 | 250 |
| 0.5 | 100 + 50 + 100 | 83 | 250 + 100 + 250 | 200 |
| 24 | 125 + 100 + 350 | 255 | 250 + 125 + 250 | 245 |
| 48 | 5 + 5 + 130 | 13 | 20 + 100 + 250 | 155 |

[1]Three different trials were carried out.
[2]A 254 nm λ UV radiation source was used.
[3]The weight (mg/L) was obtained as a pellet from the bacterium.

Example 2: Extract Preparation

After the relevant period of time for each sample, the *A. ferroxidans* culture samples exposed to UV radiation were taken and subjected to centrifugation at approximately 10,000×g (13,000 RPM) for 5 minutes at 4° C. The centrifugation process was repeated three times for each sample. The supernatant was discharged and the pellet was saved to be used immediately; otherwise, the pellet was kept at −25° C., until use.

The pellet was dried under vacuum in a lyophilizer at −40° C. and pulverized. The pulverized pellet was mixed with sterilized de-ionized water in order to obtain different concentrations of pellet material (0.05 g/mL, 0.10 g/mL, 0.15 g/mL, 0.20 g/mL, and 0.25 g/mL). 0.25 g/mL or higher concentrations of the extract may be preferable because more extract material generally provides a greater protective effect. However, increases in protective effect may be negligible in some uses above certain concentrations. Further, smaller concentrations may be desirable in some uses, particularly if the extract has negative side-effects in that use.

Example 3: UV Protection Testing

UV radiation is know to kill prokaryotic and simple eukaryotic cells. Accordingly, a decrease in cell death for these cells when exposed to UV radiation in the presence of a material indicates that the material is a UV protectant and blocks UV radiation. Cell death tests were performed using prokaryotic cells such as *Bacillus subtilis* (wild type isolated from the Prairie View A&M University farm), *Staphylococcus aureus* (ATCC 6538), *Salmonella typhimurum* (ATCC 14028), and eukaryote cells such as *Saccharomyces cerevisiae* (ATCC 66348).

The bacterial cells were grown in nutrient broth and/or nutrient agar plates (Difco, Detroit, Mich.) and the yeast cells were grown in yeast extract nutrient broth and/or agar plates. The microbial cultures were incubated at 30° C., and used after 24 hours for bacteria and after 48 hours for yeast. Microbial cells were used during exponential growth, and their population was measured by optical density reading (O.D.) at 600 nm. Different O.D. were used (0.3, 0.5, 0.8, and 1.0), however, 0.5 was preferred because cells were in exponential growth at this OD and not near the end of it.

From each bacterial solution, different fresh dilutions (10, 100, 1,000, 10,000, and 1,000,000 cells/mL) were prepared, but 10,000 cells/mL dilution was preferred because it assured sufficient cell density, but did not reach non-exponential growth stages too early. Twenty mL from each dilution were separately transferred to sterile 9 cm Petri plates. Three replicates for each bacterial or yeast dilution were exposed to shortwave (254 nm) or longwave (350 nm) UV radiation for different lengths of time (15, 30 or 60 minutes). However, bacterial or yeast exposure to shortwave UV radiation for 60 minutes was preferred because it represents harsher conditions that longwave radiation and shorter time periods. Shortwave UV radiation is known to be more lethal to most organisms than longwave UV radiation. Bacterial or yeast cultures were exposed alone (control) or in mixture with the pulverized *A. ferroxidans* pellet extract from Example 2 (treatment). Different concentrations of the extract (0, 150, 200, or 250 mg/mL) were used. However, 250 mg/mL was preferred and was used to obtain the data presented in TABLES 2-4. The mixture was always well stirred in order to ensure complete mixing of the bacterial or yeast cells with the extract. In addition to control (bacteria or yeast alone), different types of extract treatments were used:

1) *Bacillus subtilis* (wild type)

2) *B. subtilis*+Extract of *A. ferroxidans* (from 4-week-old culture)

3) *B. subtilis*+Extract of *A. ferroxidans* (from 2-week-old culture)

4) *Salmonellas typhimurum* (ATCC 14028)

5) *S. typhimurum* (ATCC 14028)+Extract of *A. ferroxidans* (from 4 week-old culture)

6) *S. typhimurum* ATCC 14028+Extract of *A. ferroxidans* (from 2 week-old culture)

7) *Staphylococcus aureus* (ATCC 6538)

8) *S. aureus* (ATCC 6538)+Extract of *A. ferroxidans* (from 4-week-old culture)

9) *S. aureus* (ATCC 6538)+Extract of *A. ferroxidans* (from 2-week-old culture)
10) *Saccharomyces cerevisiae* (ATCC 66348)
11) *S. cerevisiae* (ATCC 66348)+Extract of *A. ferroxidans* (from 4 week-old culture)
12) *S. cerevisiae* (ATCC 66348)+Extract of *A. ferroxidans* (from 2 week-old culture)
13) *C. albicans*
14) *C. albicans*+Extract of *A. ferroxidans*

After exposure of the liquid microbial cultures to UV irradiation, 1 mL of the UV-irradiated microbial dilutions (10,000 cells/mL) was placed into the center of a sterile Petri dish, and agar media (nutrient agar for bacterial cultures or yeast extract agar for yeast) was poured into the Petri dish, thus following the standard pour plates technique. Two different size of Petri dishes were used: 1) standard plain 9 cm diameter, and 2) a 9 cm diameter Petri dish divided into three equal areas. A minimum of six replicates per dilution were made. The microbial cultures were immediately incubated at 30° C. Microbial growth was determined and counted after 24, 48, 60, and 72 hours and after one week. Microbial growth was determined by using the standard counting of the number of colony forming units (CFU) of the UV-irradiated or non-irradiated microbial cultures.

The results as indicated in TABLES 2-4 clearly demonstrate the UV protection that *A. ferroxidans* extract provides to *S. cerevisiae, C. albicans*, and *B. subtilis*. Similar results were obtained using the other organisms in the list above.

TABLE 2 shows prolific growth of *S. cerevisiae* in all the plates with yeast culture that were also previously treated with the extract of *A. ferroxidans*, and exposed to UV radiation for 1 hour, and later incubated at 30° C. for 72 hours. All plates were fully covered by the yeast. In contrast, yeast cultures that were not treated with the extract of *A. ferroxidans* did not show substantial growth at all, thus indicating that the cells were not protected from the UV radiation and were killed. This indicates that the extract of *A. ferroxidans* is able to protect eukaryote cells such as yeast cells from UV damage. Therefore, the extract of *A. ferroxidans* should be effective to protect other eukaryote cells such as mammalian cells against UV radiation.

TABLE 2

Protection Against UV Radiation by *A. Ferroxidans* Extract in Cultures of *S. Cerevisiae*

| | Colony Count | | | | |
|---|---|---|---|---|---|
| Treatment | Plate 1 | Plate 2 | Plate 3 | Mean | STDEV |
| SAC[3] only (control) | FC[1] | FC | FC | N/A | N/A |
| Sac + UV | 0 | 0 | 1 | 0.33 | 0.58 |
| SAC + EAF[2] | FC | FC | FC | N/A | N/A |
| SAC + EAF + UV | FC | FC | FC | N/A | N/A |

[1]FC = Agar plates fully covered by microbial growth.
[2]EAF = Extract from *Acidithiobacillus ferroxidans*.
[3]SAC = *Saccharomyces cerevisiae*.

TABLE 3 and FIG. 4 show the protective effect *A. ferroxidans* extract against UV radiation in a different yeast, *C. albicans*. The *A. ferroxidans* extract gave full protection to *C. albicans* growing at 30° C. for 72 hours. *C. albicans* with *A. ferroxidans* extract was exposed to UV radiation for 1 hour, then incubated at 30° C. for 72 hours and no UV radiation. The yeast grew as much (95-100%) as the non-UV treated yeast cultures. However, all UV-treated cultures without the protective *A. ferroxidans* extract showed no growth at all. This corroborates the protective effect of the *A. ferroxidans* extract against UV radiation in a different eukaryotic cell, *C. albicans*.

TABLE 3

Protection Against UV Radiation by *A. Ferroxidans* Extract in Cultures of *C. Albicans*

| | Colony Count | | | | |
|---|---|---|---|---|---|
| Treatment | Plate 1 | Plate 2 | Plate 3 | Mean | STDEV |
| CA[1] only (control) | 103 | 91 | 89 | 94.33 | 7.57 |
| CA + UV | 0 | 0 | 0 | 0.00 | 0.00 |
| CA + EAF[2] | 101 | 94 | 104 | 99.67 | 5.13 |
| CA + EAF + UV | 92 | 107 | 82 | 93.67 | 12.58 |

[1]CA = *Candida albicans*.
[2]EAF = Extract from *Acidithiobacillus ferroxidans*.

TABLE 4 shows the marked protective effect of *A. ferroxidans* extract against UV radiation in a prokaryote cell such as *Bacillus subtilis*. The results show great growth of the bacterium fully covering the plates in those cultures treated with the *A. ferroxidans* extract, as compared to those plates that were not treated and which showed no bacterial growth. All plates were exposed to UV irradiation for 1 hour and then incubated without UV radiation for 72 hours. These results indicate the efficacy of *A. ferroxidans* extract in protecting bacterial cells as well.

TABLE 4

Protection Against UV Radiation by *A. Ferroxidans* Extract in Cultures of *B. Subtilis*

| | Colony Count | | | | |
|---|---|---|---|---|---|
| Treatment | Plate 1 | Plate 2 | Plate 3 | Mean | STDEV |
| BS only (control) | FC[1] | FC | FC | N/A | N/A |
| BS[2] + UV | 0 | 2 | 0 | 0.67 | 1.15 |
| BS + EAF[3] | FC | FC | FC | N/A | N/A |
| BS + EAF + UV | FC | FC | FC | N/A | N/A |

[1]FC = AGAR Plates fully covered.
[2]BS = *Bacillus subtilis*.
[3]EAF = Extract from *Acidithiobacillus ferroxidans*.

Example 4: Effects of UV Protective Agent on *S. Cerevisiae* Stress Response Gene Expression The effects of the *A. ferroxidans* extract to protect yeast against UV damage were further confirmed by evaluating the expression of five genes, which encode zinc finger proteins, known to be involved in chromosomes repair, after exposure to damage by different stressing factors including UV radiation. The genes were expressed in *S. cerevisiae* (ATCC 66348). The semi-quantitative real time polymerase chain reaction (qRT-PCR) was used for analysis.

*S. cerevisiae* previously treated with the *A. ferroxidans* extract were grown for 2-4 days in liquid cultures at 26-30° C. see as described above. Control cell were not treated with the *A. ferroxidans* extract. Two hundred mL of yeast cultures were grown in 500 ml flasks, each, under shaking conditions (350 RPM). Six replicates were used for each yeast culture. After 2-4 days incubation, cells were harvested and subjected to centrifugation to obtain a pellet. Fifty mL of yeast culture sample were used in four replicates each. Cells were centrifuged three times at 15,000 RPM, under refrigeration (4° C.) for 10 minutes three times. Cells were harvested as pellets, and the pellets were kept under freezing conditions (−80° C.) or used immediately for further analysis.

For each pellet, the quantity and quality of the total RNA was determined by UV spectroscopy, using the a Nano-Drop™ spectrophotometer. cDNA was synthesized from total RNA with a combination of random hexamers and oligo dT and Superscript III®. cDNA was also synthesized with oligo dT only and Superscript II®. After cDNA synthesis, the RNA was digested with RNase H. SYBR green was used for real time detection of the PCR products in the 7900HT Sequence Detection System.

PCR amplification primers were designed for each gene of interest, as follows:

| S. cerevisiae gene | primers (listed 5' to 3') | Amplicon Size |
|---|---|---|
| dnaX-F | TGGAAGCTGAAGCCGGG (SEQ ID NO. 1) | 122 |
| dnaX-R | AGAAACAAGAGCAATTTTTCCCC (SEQ ID NO. 2) | |
| Msn4p-F | CGAAAGTGGCGACTACAGGC (SEQ ID NO. 3) | 111 |
| Msn4p-R | ATATTCATTTGATGATGATGGAAAGATCG (SEQ ID NO. 4) | |
| recA-F | TACGGATTTTTCTGGTGG (SEQ ID NO. 5) | 101 |
| recA-R | CTGCAACACCAAATTGGTCG (SEQ ID NO. 6) | |
| ruvB-F | GCAGTTACGAGAACTGCGGC (SEQ ID NO. 7) | 91 |
| ruvB-R | CAACAAACCCTCCTTCAACCC (SEQ ID NO. 8) | |
| GAPDH-F | AACACCCATGACGAACATTGG (SEQ ID NO. 9) | 81 |
| GAPDH-R | CAAAAGCACATTGACGCTGG (SEQ ID NO. 10) | |

Conditions were developed for the amplification of each target gene by RT-PCR using genomic DNA as a template. The expression level of each gene including GAPDH was determined from each sample in triplicate. A reference standard curve for each gene was generated and each point was measured in triplicate. Positive controls using genomic DNA and negative controls with cDNA synthesis reactions where the reverse transcriptase was omitted and water only were included in assays. Samples were amplified in the 7900HT Sequence Detection System at 95° C. for 10 min. followed by 50 cycles at 95° C. for 30 sec., 60° C. for 30 sec., and 72° C. for 30 sec. Fluorescence measures were made at the end of each extension cycle. Following PCR amplification, a melting curve analysis was performed by heating the samples at 95° C. for 15 sec., and 95° C. at 1 C/min.

After PCR amplification and melting curve analysis, a Ct value was calculated for each sample. The relative amount of RNA was determined comparing the Ct value of the test samples to the control sample after normalization with GAPDH. Ct values for any given sample were only used if their value fell within the standard curve for each gene. Otherwise, the assay was repeated and the test sample (i.e. cDNA) was diluted.

Several methods were tested for isolating and purifying total RNA from S. cerevisiae. These methods include the RNAeasy Mini Kit™ (Qiagen), TRI Reagent™ (Sigma), Master Pure Complete DNA and RNA Purification Kit™ (Epicentre Biotechnologies Inc.), hot phenol:chloroform:isoamyl (Sigma) and modifications of some of these protocols. The following modified RNAeasy™ protocol was successfully used to isolate total RNA from S. cerevisiae.

Frozen cellular pellets were thawed, thoroughly mixed with 2-3 volumes RNA Protect™ (Qiagen) and incubated for 10 min. at 23° C. Cells were centrifuged at 5,000×g for 10 min at 23° C. Supernatant was decanted and discarded. Cell pellets were resuspended in 200 ul 15 mg/mL lysozyme and 1.5 mg/mL proteinase K in 10 mM TRIS-HCl (pH 7.4) and 1 mM EDTA. Cells were incubated for 10 min. at 23° C. Seven hundred μL RLT buffer were added and mixed by vortexing. Samples were sonicated for 1 min. Four hundred seventy μL ethanol were added and mixed by vortexing. The solution was applied to a resin spin-column. The spin-column was centrifuged at 8,000×g for 10 sec. at 23° C. Flow-through was discarded, and the remaining solution was added and centrifuged as above. Eighty μL of DNase solution was applied (70 μL RDD buffer and 10 μL DNase) to the spin-column and incubated for 15 min. at 23° C. Three hundred and fifty μL RW1 buffer was applied to the spin-column solution. The spin-column solution was centrifuged at 8,000×g for 1 min. at 23° C. Flow-through was discarded. Five hundred μL RW1 was applied to the spin-column. The spin-column was centrifuged at 8,000×g for 1 min. at 23° C. Flow-through was discarded. Use of the spin-column was repeated. The spin-column was transferred into a new collection tube and centrifuged at 8,000×g for 1 min. at 23° C. The spin-column was transferred into a new collection tube. Fifty μL of RNase-, DNase-free water was added to the center of the spin-column and left at 23° C. for 1-2 min. The spin-column was centrifuged at 8,000×g for 1 min. at 23° C. The flow-through was saved, because it contained the RNA. The quantity and quality of the RNA was evaluated by absorbance spectroscopy and agarose gel electrophoresis.

After RNA was isolated from the cells, the samples were analyzed for gene expression by RT-PCR, as described above. cDNA was synthesized with oligo dT, as described above. A Northern Blot showed that stress response genes were not significantly up-regulated after UV exposure in S. cerevisiae previously exposed to the A. ferroxidans extract. No significant differences were seen in the total RNA for the cells.

Differences in expression for Msn4pn and ruvB, which are involved in chromosome repair after stress-related damage, were observed between samples of S. cerevisiae treated with the A. ferroxidans extract and those not treated after the samples were exposed to UV radiation as described above.

Results of further experiments regarding stress-response gene expression in S. cerevisiae are shown in TABLE 5. In TABLE 5, "SA" designates control S. cerevisiae that were not treated with bacterial extract and not exposed to UV radiation. "S5" designates S. cerevisiae treated with bacterial extract and exposed to UV radiation for 48 hours. "S6" designates S. cerevisiae treated with bacterial extract and exposed to UV radiation for 72 hours.

TABLE 5

Stress-Response Gene Expression in *S. cerevisiae*

| | Msn4p (Ct) | recA (Ct) | ruvB (Ct) | GAPDH (Ct) |
|---|---|---|---|---|
| SA (1:50 cDNA) - 1 | 35.015858 | 31.099762 | 34.97601 | 25.63601 |
| SA (1:50 cDNA) - 2 | 34.556225 | 31.193922 | 34.43322 | 25.67667 |
| SA (1:50 cDNA) - 3 | 34.61304 | 31.48071 | 33.99136 | 25.86641 |
| SA (1:50 cDNA) - Mean | 34.7 | 31.3 | 34.5 | 25.7 |
| SA (1:50 cDNA) - Std. Dev. | 0.25 | 0.20 | 0.49 | 0.12 |
| SA (1:50 cDNA) - Std. Error | 0.14 | 0.11 | 0.28 | 0.07 |
| S5 (1:50 cDNA) - 1 | 48.143795 | 36.857708 | 39.42146 | 33.32396 |
| S5 (1:50 cDNA) - 2 | 38.14609 | 37.113995 | 40.3668 | 32.55367 |
| S5 (1:50 cDNA) - 3 | 39.83437 | 36.967648 | 39.43715 | 33.174426 |
| S5 (1:50 cDNA) - Mean | 42.0 | 37.0 | 39.7 | 33.0 |
| S5 (1:50 cDNA) - Std. Dev. | 5.35 | 0.13 | 0.54 | 0.41 |
| S5 (1:50 cDNA) - Std. Error | 3.09 | 0.07 | 0.31 | 0.24 |
| S6 (1:50 cDNA) - 1 | 34.409473 | 31.552845 | 34.38703 | 25.48201 |
| S6 (1:50 cDNA) - 2 | 34.430233 | 31.288467 | 34.8099 | 25.45857 |
| S6 (1:50 cDNA) - 3 | 35.021397 | 31.782907 | 34.67211 | 25.69369 |
| S6 (1:50 cDNA) - Mean | 34.6 | 31.5 | 34.6 | 25.5 |
| S6 (1:50 cDNA) - Std. Dev. | 0.35 | 0.25 | 0.22 | 0.13 |
| S6 (1:50 cDNA) - Std. Error | 0.20 | 0.14 | 0.12 | 0.07 |
| S5 (1:5 cDNA) - 1 | 38.55734 | 32.21721 | 37.2342 | 30.968388 |
| S5 (1:5 cDNA) - 2 | 37.911972 | 32.550484 | 37.835094 | 30.854069 |
| S5 (1:5 cDNA) - 3 | 37.23461 | 33.667084 | 40.251022 | 30.989134 |
| S5 (1:5 cDNA) - Mean | 37.9 | 32.8 | 38.4 | 30.9 |
| S5 (1:5 cDNA) - Std. Dev. | 0.66 | 0.76 | 1.60 | 0.07 |
| S5 (1:5 cDNA) - Std. Error | 0.38 | 0.44 | 0.92 | 0.04 |
| S6 (1:5 cDNA) - 1 | 35.528088 | 32.005764 | 35.446632 | 26.329565 |
| S6 (1:5 cDNA) - 2 | 35.120403 | 31.908882 | 36.131447 | 26.248236 |
| S6 (1:5 cDNA) - 3 | 35.390247 | 31.86025 | 35.302666 | 26.37515 |
| S6 (1:5 cDNA) - Mean | 35.3 | 31.9 | 35.6 | 26.3 |
| S6 (1:5 cDNA) - Std. Dev. | 0.21 | 0.07 | 0.44 | 0.06 |
| S6 (1:5 cDNA) - Std. Error | 0.12 | 0.04 | 0.26 | 0.04 |

Example 5: Identification of Protein Expression Changes in *S. Cerevisiaea* in Response to UV Radiation Yeast cells were grown in yeast extract agar media at 28-30° C., overnight, following microbiological standard procedures. The best grown colonies were selected to make culture dilutions, which were used as a source of inoculum in liquid culture. Different yeast dilutions were then made, and their concentrations were measured according to the absorbance (optical density=O.D) at 550-600 nm wavelength). Different dilutions were used: 0.05, 0.02, 0.01, 0.0005 O.D. However, dilution 0.01 O.D was preferable.

Yeast cultures were then exposed to UV radiation for 48 hours an incubated at 28° C., then samples were taken to determine protein expression. Samples were taken and mixed with phosphate buffer saline solution (PBS), pH 7.4 following standard procedures (Sambrook, F., and Maniatis. 1989. Molecular cloning: A laboratory manual. 2nd edition, Cold Spring Harbor Laboratory Press. Cold Spring Harbor, N.Y. Volume 3, appendix B, 12; Medicago AB. 2009.) The mixture of yeast culture and PBS were subjected to centrifugation at 4° C. at 1500 RPM for 5 minutes three times, and the supernatants were discarded each time. One gram of final pellets were stored at −80° C. until use, otherwise, the pellets were used immediately. Two samples were used for analysis by two-dimensional difference gel electrophoresis (2D DIGE) and protein identification by liquid chromatography tandem mass spectrometry (LC-MS/MS). Six proteins with increased or decreased expression are identified in TABLE 6.

TABLE 6

*S. Cerevisiaea* Proteins Up-Regulated or Down-regulated by UV Exposure

| Protein | Accession # | Change |
|---|---|---|
| Heat shock protein SSB1 | P10591.4 GI:417149 | Increased |
| Protein disulfide isomerase | P17967.2 GI:129732 | Decreased |
| Alpha-glucosidase MAL12 | P53341.1 GI:1708906 | Decreased |
| Methyl tetrahydropteroyl triglutamate | P05694.4 GI:730018 | Decreased |
| NADH-cytochrome b5 reductase 2 | P36060.1 GI:549725 | Increased |
| NADP-specific glutamate dehydrogenase | P07262.2 GI:2506355 | Increased |
| Superoxide dismutase | P00447.1 GI:134681 | Increased |
| Hexokinase 1 | P04806 GI:1170444 | Increased |
| Fructose-bisphosphate aldolase | P14540.3 GI:113626 | Decreased |
| Phosphate glycerate mutase | P00950.3 GI:548534 | Increased |
| Glucokinase 1 | P17709.1 GI:123899 | Decreased |

Example 6: Identification of Protein Expression Changes in *A. ferroxidans* in Response to UV Radiation A culture of *A. ferroxidans* was exposed to UV radiation for 72 hours. Samples were taken and analyzed for protein as described in Example 5. Results are presented in TABLE 7.

TABLE 7

*A. ferroxidans* Proteins Up-Regulated or Down-regulated by UV Exposure

| Protein | Accession # | Change |
|---|---|---|
| Major outer membrane protein 40 | CAA10107.1 | Increased |
| RuBisCO large subunit 1 | P0C916.1 | Increased |
| RuBisCO large subunit 2 | P0C917.1 | Increased |
| Phosphoribulokinase | ACK78673.1 | Increased |
| Ribosomal protein S2 | ACK79803.1 | Increased |
| Ketol-acid reductoisomerase | B5EP52.1 | Increased |
| Pyridine nucleotide-disulfide | ACK80497.1 | Increased |
| Hsp20 | ACK78444.1 | Decreased |
| Methionine synthase | B5ELU7.1 | Increased |
| Serine hydroxymethyltransferase | ACK78912.1 | Increased |
| Chaperonin | ACK77997.1 | Decreased |
| HSP70 | B5ENA3.1 | Decreased |

Example 7: Identification of cDNA Changes in *A. ferroxidans* in Response to UV Radiation A culture of *A. ferroxidans* was exposed to UV radiation for 72 hours. Samples were centrifuged to prepare pellets, which were frozen. Pellets were subject to Real Time PCR. Primers and genes thus identified were as follows:

| Gene | Amplicon Size | Forward primer (5'-3') | Reverse Primer (5'-3') |
|---|---|---|---|
| ccbL2 (P0C917.1) | 117 | GCCGGAAGCTGGGATGCACA (SEQ ID No. 11) | GAAGCGCACCGTGGCCTGAT (SEQ ID No. 12) |
| cbbP (ACK78673.1) | 94 | CAGCGCACCTGGCACCTTCA (SEQ ID No. 13) | GCCCGTCTTCACGCCACCAT (SEQ ID No. 14) |
| rpsB (ACK79803.1) | 100 | CACGGCGCTCAGCTTTGTCG (SEQ ID No. 15) | AGCTTCCTGCTCGACGGCCT (SEQ ID No. 16) |
| AFE_2086 (CK78444.1) | 126 | CCCCTGGATGGTAAGCACCC CT (SEQ ID No. 17) | GATTGGTCGCCCCGCGTTGA (SEQ ID No. 18) |
| metE (B5ELU7.1) | 158 | TGGTGGGGAAGGCAGGCAG T (SEQ ID No. 19) | AGCCGTCGCCTCACGCAAAA (SEQ ID No. 20) |
| glyA (ACK78912.1) | 71 | GGACCGTGCGCTGGAGCTTT (SEQ ID No. 21) | GATTGGCCTGCGAGCCGGAA (SEQ ID No. 22) |
| groES (ACK77997.1) | 83 | ATGGCCGGCAGCGACGATTT (SEQ ID No. 23) | AGCAGAAGACTGCCGGTGG GA (SEQ ID No. 24) |
| dnaK (B5ENA3.1) | 138 | GGCGCGGGTCAGCTTCATGT (SEQ ID No. 25) | GCCATGCAGCGCCTGAAGGA (SEQ ID No. 26) |
| gap (ACK78716.1) | 128 | TTTCTTGGCGCCGCCCTTGA (SEQ ID No. 27) | TGCTTGCCGAACGCGATCCT (SEQ ID No. 28) |
| rpoC (ACK80911.1) | 83 | TGTCGCTGGAGGCGCAGTTG (SEQ ID No. 29) | AACGGGCTCACCATTGGCCG (SEQ ID No. 30) | cDNA levels for ccbL2 (ribulose bisphosphate carboxylase, large subunit 2, abbreviated RuBisCO sumunit 2) and metE (methyltransferase), increased by 20% following UV-exposure. cDNA levels for dnak (chaperone protein Dnak), glyA (serine hydromethyltransferase) and rpsB (ribosomal protein s2) decreased by between 60% and 70%.

Example 8: Transfection of *S. Cerevisiaea* to Increase UV-Resistance

*S. Cerevisiaea* were transfected with the plasmid shown in FIG. 1 (3 genes), with a similar plasmid containing only HSP70, ADH, or hesokinase, or with an identical plasmid lacking the riboswitch component (3 genes-). Transfected yeast cells were grown in yeast extract agar plates at 28-30° C., overnight. Culture solutions were made and inoculated into 250 ml yeast extract liquid media contained in a 1 liter sterile glass bowl. Thus, the initial working concentration of the yeast cells cultures were equivalent to an optical density (O.D) of 0.07 at 600 nm. pH of cultures were adjusted to 4-4.5; the experiments were set up in triplicates. The yeast cultures were incubated under alternate regimes of 12 hours of no-UV radiation and 48 hours of UV-radiation (254 nm), and continued shake (300 RPM), a total of 60 hours incubation at 28-30° C. Incubation was completely covered and protected against any kind of light from outside. Markers of cell growth were measured and results are reported in TABLE 8. Control yeast were not transfected.

TABLE 8

Growth Markers in UV-Resistant *S. Cerevisiaea*

| Sample | UV | OD | DNA (ng/μL)* | RNA (ng/μl)* | ATP (RLU) |
|---|---|---|---|---|---|
| 3 genes | Y | 1.108 | 154 ± 8.2 | 120.9 ± 6.8 | 93 ± 9 |
| 3 genes | N | 0.580 | 53.5 ± 2.8 | 19.4 ± 1.1 | 115 ± 20 |
| 3 genes - | Y | 1.217 | 85.5 ± 1.2 | 60.8 ± 3.1 | 89 ± 17 |
| 3 genes - | N | 0.571 | 19.7 ± 1.5 | 5.5 ± 1.2 | 97 ± 12 |
| HSP70 | Y | 1.119 | 98.5 ± 0.2 | 117.2 ± 2.3 | 105 ± 13 |
| HSP70 | N | 0.564 | 9.7 ± 0.85 | 15.8 ± .92 | 120 ± 17 |
| ADH | Y | 1.109 | 126 ± 5.1 | 110.2 ± 3.1 | 121 ± 14 |
| ADH | N | 0.601 | 5.7 ± 1.2 | 24.5 ± 0.5 | 155 ± 12 |
| Hexokinase | Y | 1.098 | 84 ± 4.2 | 80.5 ± 1.5 | 81 ± 22 |
| Hexokinase | N | 0.519 | 7.2 ± 1 | 7.8 ± 1.15 | 57 ± 11 |
| Control | Y | 0.532 | 80.2 ± 2.5 | 42.3 ± 1.4 | 87.9 ± 12.1 |
| Control | N | 0.435 | 8.9 ± 1.4 | 14.3 ± 1.7 | 102 ± 15 |

*Mean +/- standard deviation
OD—Optical density;
ATP—Adenosine triphosphate;
RLU—Relative luminescence units Example 9: Fermentation Using UV-Resistant *S. Cerevisiaea*

*S. Cerevisiaea* were transfected with the plasmid similar to that of FIG. 1, containing only HSP. Yeast were cultured and then exposed to UV radiation for 48 hours. Fermentation products in the yeast were then measured using HPLC. Results for glucose production are shown in TABLE 9.

TABLE 9

Glucose Production in UV-Resistant *S. Cerevisiaea*

| Sample | UV | Glucose (g/L) |
|---|---|---|
| HSP + Yeast | Y | 63.92 +/- 7.92 |
| HSP + Yeast | N | 606.32 +/- 72.10 |

TABLE 9-continued

Glucose Production in UV-Resistant *S. Cerevisiaea*

| Sample | UV | Glucose (g/L) |
|---|---|---|
| Control | Y | 0 |
| Control | N | 0 |

Increased inositol production was also observed.

Example 10: Protection of Watermelons from UV Damage by *A. ferroxidans* Extract An extract was prepared from an *A. ferroxidans* culture previously exposed to UV-radiation for 72 hours. Sans Pepins wateremelon fruits were cleaned in sterile water and dried with a paper towel. The watermelons were then coated with different concentrations of bacterial extract (0.1, 0.2, 0.5, 0.7 and 1%) using a small brush or by spraying until their entire surfaces were covered. Watermelons were then placed in a Percival environmentally-controlled chamber (Percival Scientific, Perry, Iowa) and exposed to 254 nm or 360 nm UV radiation at a temperature of 27-29° C. and 85% relative humidity for two weeks. Control watermelons coated with water were also tested.

Watermelons were assed for color and shape of the fruit rind, blistering of the watermelon fruit, color and ripening (texture) of the flesh of the fruit, and content of glucose, carotene, and lycopene.

Flesh color was assigned the following values: 1=pale, 2=pale red, 3=medium red, 4=dark red.

Firmness (textures) was assigned the following values: 1=hard, 2=medium hard, 3=soft, 4=very soft.

Blistering was assigned the following values: 0%=no blistering, 1=10% blistering, 2=25% blistering, 3=50% blistering, 4=75-100% blistering.

Rind color was assigned the following values: 1=very dull green, 2=dull light green, 3=medium green, 4=very (bright) green Glucose, carotene, and lycopene content were determined using HPLC.

Results are presented in TABLES 10 and 11.

TABLE 10

Effects of Extract on Watermelon Color, Blistering, Flesh Color, and Flesh Texture

| Sample | Rind Color | Blistering | Flesh Color | Flesh Texture |
|---|---|---|---|---|
| Extract + UV | 4 | 0 | 3 | 3 |
| Water + UV | 2 | 2 | 2 | 4 |

TABLE 11

Effects of Extract on Watermelon Glucose, Lycopene, and Carotene Content

| Sample | Glucose (g/L) | Carotene (mg/L) | Lycopene (mg/kg) |
|---|---|---|---|
| Extract + UV | 13.00 +/0.90 | 20.40 +/− 1.64 | 47.87 +/− 5.14 |
| Water + UV | 12.07 +/− 0.75 | 45.17 +/− 7.73 | 27.07 +/− 3.64 |

Example 11: Protection of Fibroblasts from UV Damage by *S. Cerevisiaea* Extract

*S. Cerevisiae* cells were transfected with the plasmid of FIG. 1. Extracts of these yeast were applied to fibroblast cultures (which are indicative of skin protection), which were then exposed to UV radiation. Fibroblast cells were then stained for indicators of apoptosis (staining method differentiates between live and dead cells) and cell numbers were counted using microscopy. Control samples were not treated or were treated with extract from non-transfected yeast. Results are presented in TABLE 12.

TABLE 12

Effects of Extract on Fibroblast Resistance to UV-Radiation

| Sample | UV | % Apoptosis | Cell count |
|---|---|---|---|
| Fibroblasts | N | 0 | 15 alive, 1 dead |
| Fibroblasts | Y | 78.7 | 18 alive, 7 dead |
| Fibroblasts + Transfected Extract | Y | 0 | 18 alive, 2 dead |
| Fibroblasts + Non-transfected Extract | Y | 0 | 17 alive, 4 dead |

Example 12: Solubility and Toxicity Data

Extracts from *S. Cerevisiae* and *A. ferroxidans* were tested to determine their solubility in water and their toxicity. Results are presented in TABLE 13.

TABLE 13

Solubility and Toxicity Data

| Extract | Solubility mg/ml | Toxicity ($LD_{50}$) mg/Kg |
|---|---|---|
| *S. ceresiviae* + no UV | 0.05 | 88.3-100 |
| *S. ceresiviae* + UV | 0.015 | 100 |
| *A. ferroxidans* + UV | 0.15 | 100 |

Water solubility may be important for various reasons depending on the use. For example, in methods where the extract is applied to a fruit or vegetable, good water solubility means that the extract should be largely removed when the fruit or vegetable is washed, decreasing the risk of any safety hazards for consumers. Good water solubility also indicates that keeping the extract in solution and thereby benefiting from its protective effects during a fermentation process may be easier.

Toxicity is significant because it indicates the likelihood of any adverse effects from the extracts if they are consumed. A high $LD_{50}$ value indicates that more of the extract may be consumed without adverse effects. In general, the extract may be used so that the amount present on a fruit or vegetable or in portion of a fermentation product typically consumed is less than the $LD_{50}$.

Although only exemplary embodiments of the invention are specifically described above, it will be appreciated that modifications and variations of these examples are possible without departing from the spirit and intended scope of the invention. For example, throughout the specification particular measurements are given. It would be understood by one of ordinary skill in the art that in many instances particularly outside of the examples other values similar to, but not exactly the same as the given measurements may be equivalent and may also be encompassed by the present invention. As another example, although only monocultures of particular microbes are described herein for extract production, it will be understood that co-cultures are possible and may provide the benefit of different sources of UV-blocking components in the same extract.

The invention claimed is:

1. A method of preparing a UV-blocking composition comprising:
exposing a culture of yeast transfected with a nucleic acid encoding at least the following proteins in the following order: a heat shock protein, an alcohol dehydrogenase protein and a hexokinase protein to UV radiation for a length of time sufficient to induce production of a UV-blocking cellular material in the yeast in response to the UV radiation; and extracting UV-blocking cellular material comprising protein produced in response to the UV radiation from the yeast, wherein the nucleic acid encoding the proteins is under control of a promoter.

2. The method of claim 1, wherein the yeast comprises S. Cerevisiaea.

3. The method of claim 1, wherein extracting comprises centrifuging the yeast culture under conditions sufficient to precipitate UV-blocking cellular proteins.

4. The method of claim 1, wherein the UV radiation comprises short wave UV radiation, long wave radiation, or a combination of both.

5. The method of claim 1, wherein exposing the culture of yeast to UV radiation is for a time not sufficient to substantially kill the yeast in the culture and the method further comprises ceasing exposure to UV radiation, then continuing to culture the yeast subsequent to exposing it to UV radiation and prior to extracting.

6. The method of claim 1, wherein extracting comprises pelletizing the culture of yeast in a centrifuge to form an extract pellet.

7. The method of claim 1, wherein extracting comprises evaporating a culture medium containing the culture of yeast.

8. The method of claim 1, wherein extracting comprises isolating a protein from the culture of yeast.

9. The method of claim 1, further comprising forming a composition comprising the UV-blocking cellular material in a concentration between approximately 0.05 g/mL and 0.025 g/mL.

10. The method of claim 1, further comprising formulating the UV-blocking cellular material in a carrier to form a composition.

11. The method of claim 1, wherein the UV-blocking composition blocks at least approximately 50% of UV radiation.

12. The method of claim 1, wherein the UV-blocking composition blocks at least approximately 50% of longwave UV radiation.

13. The method of claim 1, wherein the UV-blocking composition blocks at least approximately 50% of shortwave UV radiation.

14. The method of claim 1, wherein the transfected nucleic acid further includes a riboswitch that at least partially controls the expression of the encoded proteins.

15. The method of claim 1, wherein the nucleic acid further encodes at least one of the following proteins: a Msn4pn, a ruvB, a NADH-cytochrome b5 reductase 2, a NADP-specific glutamate dehydrogenase, a superoxide dismutase, or a phosphate glycerate.

16. The method of claim 1, wherein at least one heat shock protein is heat shock protein SSB1.

17. The method of claim 1, wherein at least one hexokinase protein comprises hexokinase 1.

* * * * *

SEQUENCE LISTING

<160> NUMBER OF SEQ ID NOS: 30

<210> SEQ ID NO 1
<211> LENGTH: 17
<212> TYPE: DNA
<213> ORGANISM: Artificial Sequence
<220> FEATURE:
<223> OTHER INFORMATION: Synthetic primer

<400> SEQUENCE: 1
tggaagctga agccggg                                                  17

<210> SEQ ID NO 2
<211> LENGTH: 23
<212> TYPE: DNA
<213> ORGANISM: Artificial Sequence
<220> FEATURE:
<223> OTHER INFORMATION: Synthetic primer

<400> SEQUENCE: 2
agaaacaaga gcaattttc ccc                                            23

<210> SEQ ID NO 3
<211> LENGTH: 20
<212> TYPE: DNA
<213> ORGANISM: Artificial Sequence
<220> FEATURE:
<223> OTHER INFORMATION: Synthetic primer

<400> SEQUENCE: 3
cgaaagtggc gactacaggc                                               20

<210> SEQ ID NO 4
<211> LENGTH: 29
<212> TYPE: DNA
<213> ORGANISM: Artificial Sequence
<220> FEATURE:
<223> OTHER INFORMATION: Synthetic primer

<400> SEQUENCE: 4
atattcattt gatgatgatg gaaagatcg                                     29

<210> SEQ ID NO 5
<211> LENGTH: 18
<212> TYPE: DNA
<213> ORGANISM: Artificial Sequence
<220> FEATURE:
<223> OTHER INFORMATION: Synthetic primer

<400> SEQUENCE: 5
tacggatttt tctggtgg                                                 18

<210> SEQ ID NO 6
<211> LENGTH: 20
<212> TYPE: DNA
<213> ORGANISM: Artificial Sequence
<220> FEATURE:
<223> OTHER INFORMATION: Synthetic primer

<400> SEQUENCE: 6
ctgcaacacc aaattggtcg                                               20

<210> SEQ ID NO 7
<211> LENGTH: 20
<212> TYPE: DNA
<213> ORGANISM: Artificial Sequence

```
<220> FEATURE:
<223> OTHER INFORMATION: Synthetic primer

<400> SEQUENCE: 7
gcagttacga gaactgcggc                                            20

<210> SEQ ID NO 8
<211> LENGTH: 21
<212> TYPE: DNA
<213> ORGANISM: Artificial Sequence
<220> FEATURE:
<223> OTHER INFORMATION: Synthetic primer

<400> SEQUENCE: 8
caacaaaccc tccttcaacc c                                          21

<210> SEQ ID NO 9
<211> LENGTH: 21
<212> TYPE: DNA
<213> ORGANISM: Artificial Sequence
<220> FEATURE:
<223> OTHER INFORMATION: Synthetic primer

<400> SEQUENCE: 9
aacacccatg acgaacattg g                                          21

<210> SEQ ID NO 10
<211> LENGTH: 20
<212> TYPE: DNA
<213> ORGANISM: Artificial Sequence
<220> FEATURE:
<223> OTHER INFORMATION: Synthetic primer

<400> SEQUENCE: 10
caaaagcaca ttgacgctgg                                            20

<210> SEQ ID NO 11
<211> LENGTH: 20
<212> TYPE: DNA
<213> ORGANISM: Artificial Sequence
<220> FEATURE:
<223> OTHER INFORMATION: Synthetic primer

<400> SEQUENCE: 11
gccggaagct gggatgcaca                                            20

<210> SEQ ID NO 12
<211> LENGTH: 20
<212> TYPE: DNA
<213> ORGANISM: Artificial Sequence
<220> FEATURE:
<223> OTHER INFORMATION: Synthetic primer

<400> SEQUENCE: 12
gaagcgcacc gtggcctgat                                            20

<210> SEQ ID NO 13
<211> LENGTH: 20
<212> TYPE: DNA
<213> ORGANISM: Artificial Sequence
<220> FEATURE:
<223> OTHER INFORMATION: Synthetic primer

<400> SEQUENCE: 13
cagcgcacct ggcaccttca                                            20
```

```
<210> SEQ ID NO 14
<211> LENGTH: 20
<212> TYPE: DNA
<213> ORGANISM: Artificial Sequence
<220> FEATURE:
<223> OTHER INFORMATION: Synthetic primer

<400> SEQUENCE: 14
gcccgtcttc acgccaccat                                                  20

<210> SEQ ID NO 15
<211> LENGTH: 20
<212> TYPE: DNA
<213> ORGANISM: Artificial Sequence
<220> FEATURE:
<223> OTHER INFORMATION: Synthetic primer

<400> SEQUENCE: 15
cacggcgctc agctttgtcg                                                  20

<210> SEQ ID NO 16
<211> LENGTH: 20
<212> TYPE: DNA
<213> ORGANISM: Artificial Sequence
<220> FEATURE:
<223> OTHER INFORMATION: Synthetic primer

<400> SEQUENCE: 16
agcttcctgc tcgacggcct                                                  20

<210> SEQ ID NO 17
<211> LENGTH: 22
<212> TYPE: DNA
<213> ORGANISM: Artificial Sequence
<220> FEATURE:
<223> OTHER INFORMATION: Synthetic primer

<400> SEQUENCE: 17
cccctggatg gtaagcaccc ct                                               22

<210> SEQ ID NO 18
<211> LENGTH: 20
<212> TYPE: DNA
<213> ORGANISM: Artificial Sequence
<220> FEATURE:
<223> OTHER INFORMATION: Synthetic primer

<400> SEQUENCE: 18
gattggtcgc cccgcgttga                                                  20

<210> SEQ ID NO 19
<211> LENGTH: 20
<212> TYPE: DNA
<213> ORGANISM: Artificial Sequence
<220> FEATURE:
<223> OTHER INFORMATION: Synthetic primer

<400> SEQUENCE: 19
tggtggggaa ggcaggcagt                                                  20

<210> SEQ ID NO 20
<211> LENGTH: 20
<212> TYPE: DNA
<213> ORGANISM: Artificial Sequence
<220> FEATURE:
<223> OTHER INFORMATION: Synthetic primer
```

```
<400> SEQUENCE: 20
agccgtcgcc tcacgcaaaa                                              20

<210> SEQ ID NO 21
<211> LENGTH: 20
<212> TYPE: DNA
<213> ORGANISM: Artificial Sequence
<220> FEATURE:
<223> OTHER INFORMATION: Synthetic primer

<400> SEQUENCE: 21
ggaccgtgcg ctggagcttt                                              20

<210> SEQ ID NO 22
<211> LENGTH: 20
<212> TYPE: DNA
<213> ORGANISM: Artificial Sequence
<220> FEATURE:
<223> OTHER INFORMATION: Synthetic primer

<400> SEQUENCE: 22
gattggcctg cgagccggaa                                              20

<210> SEQ ID NO 23
<211> LENGTH: 20
<212> TYPE: DNA
<213> ORGANISM: Artificial Sequence
<220> FEATURE:
<223> OTHER INFORMATION: Synthetic primer

<400> SEQUENCE: 23
atggccggca gcgacgattt                                              20

<210> SEQ ID NO 24
<211> LENGTH: 21
<212> TYPE: DNA
<213> ORGANISM: Artificial Sequence
<220> FEATURE:
<223> OTHER INFORMATION: Synthetic primer

<400> SEQUENCE: 24
agcagaagac tgccggtggg a                                            21

<210> SEQ ID NO 25
<211> LENGTH: 20
<212> TYPE: DNA
<213> ORGANISM: Artificial Sequence
<220> FEATURE:
<223> OTHER INFORMATION: Synthetic primer

<400> SEQUENCE: 25
ggcgcgggtc agcttcatgt                                              20

<210> SEQ ID NO 26
<211> LENGTH: 20
<212> TYPE: DNA
<213> ORGANISM: Artificial Sequence
<220> FEATURE:
<223> OTHER INFORMATION: Synthetic primer

<400> SEQUENCE: 26
gccatgcagc gcctgaagga                                              20

<210> SEQ ID NO 27
```

```
<211> LENGTH: 20
<212> TYPE: DNA
<213> ORGANISM: Artificial Sequence
<220> FEATURE:
<223> OTHER INFORMATION: Synthetic primer

<400> SEQUENCE: 27
tttcttggcg ccgcccttga                                              20

<210> SEQ ID NO 28
<211> LENGTH: 20
<212> TYPE: DNA
<213> ORGANISM: Artificial Sequence
<220> FEATURE:
<223> OTHER INFORMATION: Synthetic primer

<400> SEQUENCE: 28
tgcttgccga acgcgatcct                                              20

<210> SEQ ID NO 29
<211> LENGTH: 20
<212> TYPE: DNA
<213> ORGANISM: Artificial Sequence
<220> FEATURE:
<223> OTHER INFORMATION: Synthetic primer

<400> SEQUENCE: 29
tgtcgctgga ggcgcagttg                                              20

<210> SEQ ID NO 30
<211> LENGTH: 20
<212> TYPE: DNA
<213> ORGANISM: Artificial Sequence
<220> FEATURE:
<223> OTHER INFORMATION: Synthetic primer

<400> SEQUENCE: 30
aacgggctca ccattggccg                                              20
```